(12) United States Patent
Schimpf (10) Patent No.: US 11,179,120 B2
(45) Date of Patent: Nov. 23, 2021

(54) METHODS AND SYSTEMS FOR AN X-RAY POSITIONING SYSTEM

(71) Applicant: GE Precision Healthcare LLC, Milwaukee, WI (US)

(72) Inventor: Ryan Schimpf, Saratoga Springs, UT (US)

(73) Assignee: GE Precision Healthcare LLC, Milwaukee, WI (US)

( * ) Notice: Subject to any disclaimer, the term of this patent is extended or adjusted under 35 U.S.C. 154(b) by 27 days.

(21) Appl. No.: 16/688,975

(22) Filed: Nov. 19, 2019

(65) Prior Publication Data

US 2021/0145382 A1    May 20, 2021

(51) Int. Cl.
*H05G 1/02* (2006.01)
*A61B 6/00* (2006.01)

(52) U.S. Cl.
CPC .......... *A61B 6/4441* (2013.01); *A61B 6/4476* (2013.01)

(58) Field of Classification Search
CPC ..... A61B 6/4441; A61B 6/4476; A61B 6/547; A61B 2017/00991; A61B 2034/102; A61B 2034/301; A61B 2034/303; A61B 2034/715; A61B 2034/742; A61B 34/20; A61B 34/25; A61B 34/30; A61B 34/35; A61B 34/37; A61B 34/71; A61B 34/74; A61B 46/10; A61B 6/12; A61B 6/4423; A61B 6/487; A61B 8/0841; A61B 8/12; A61B 8/4218; A61B 6/4405; A61B 90/361; A61B 6/54; A61B 6/105; A61B 6/032; A61B 6/4464; A61B 6/035; A61B 6/4085; A61B 6/4233; A61B 6/4452; A61B 6/06; A61B 6/4021; A61B 6/4429; A61B 6/4447; A61B 6/4458; A61B 6/504; A61B 6/56; A61B 6/587; A61B 6/02; A61B 6/0487; A61B 6/4241; A61B 6/548; A61B 6/102;

(Continued)

(56) References Cited

U.S. PATENT DOCUMENTS

1,438,486 A    12/1922    Gorman
3,760,916 A    9/1973    Hanks et al.
(Continued)

*Primary Examiner* — Irakli Kiknadze
(74) *Attorney, Agent, or Firm* — McCoy Russell LLP (57) ABSTRACT

Methods and system are provided for an imaging system. In one example, the imaging device, comprises a curved arm and a carrier that engages and supports the curved arm, wherein the curved arm is configured to move relative to the carrier. The imaging system further comprises a belt extending through the carrier and traversing around a periphery of the curved arm. A drive system of the imaging device comprises a motor, a drive shaft rotatably driven by the motor, and a drive pulley coupled to the drive shaft via a clutch mechanism, wherein the drive pulley is configured to rotate and engage with the belt to move the curved arm without moving the carrier, wherein the clutch mechanism is configured to switch between an engaged state and a disengaged state, wherein the engaged state comprises the driveshaft being rotatably coupled to the drive pulley and wherein the disengaged state comprises where the driveshaft is uncoupled from the drive pulley, and wherein the clutch mechanism is configured to switch between the engaged state and the disengaged state in response to a force applied to the curved arm.

19 Claims, 9 Drawing Sheets

(58) Field of Classification Search
CPC ... A61B 6/447; A61B 6/467; Y10T 74/18056; Y10T 74/18088; Y10T 74/18152; G06T 19/00; G06T 2210/41; A61G 13/04; A61G 13/06; A61G 13/08; A61G 13/10; A61G 2210/50; G01N 2223/419; G01N 23/043; G01N 23/046; A61N 5/1081; A61N 5/1082; A61N 5/10; A61N 2005/1054; A61N 2005/1056; A61N 2005/1059; A61N 2005/1061; A61N 2005/1074; A61N 2005/1094; A61N 5/1042; A61N 5/1049; A61N 7/00; A61N 1/327; G05B 2219/39135; G05B 2219/40174; G05B 2219/45119; G16H 20/40; G16H 40/63; G16H 40/67; G16H 10/60; G16H 30/20; G16H 30/40; G16H 40/00; G16H 50/20; G16H 50/50; G16H 70/20
USPC .................................................. 378/193–198
See application file for complete search history.

(56) References Cited

U.S. PATENT DOCUMENTS

| | | | |
|---|---|---|---|
| 4,987,585 A * | 1/1991 | Kidd | A61B 6/4441 378/193 |
| 6,880,691 B2 | 4/2005 | Simmons | |
| 7,052,421 B2 | 5/2006 | Simmons | |
| 7,059,463 B2 | 6/2006 | Simmons | |
| 2011/0179895 A1 * | 7/2011 | Mueller | A61B 6/4441 74/29 |

* cited by examiner

METHODS AND SYSTEMS FOR AN X-RAY POSITIONING SYSTEM

TECHNICAL FIELD

Embodiments of the subject matter disclosed herein relate to an X-ray system positioning device.

DISCUSSION OF ART

An X-ray imaging system comprising an X-ray source and an X-ray detector. X-rays emitted from the X-ray source can impinge on the X-ray detector and provide an X-ray image of an object or objects that are placed between the X-ray source and the detector. An imaging assembly may comprise a moveable support for adjusting an imaging angle and/or position.

BRIEF DESCRIPTION

In one embodiment, an X-ray system comprises a moveable arm comprising an X-ray source and an X-ray detector, wherein a drive mechanism of the arm comprises a motor, a clutch mechanism, and a drive pulley, and wherein the clutch mechanism is configured to slip in response a force applied to the moveable arm exceeding a threshold force.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present disclosure will be better understood from reading the following description of non-limiting embodiments, with reference to the attached drawings, wherein below.

DETAILED DESCRIPTION

Figure 1:
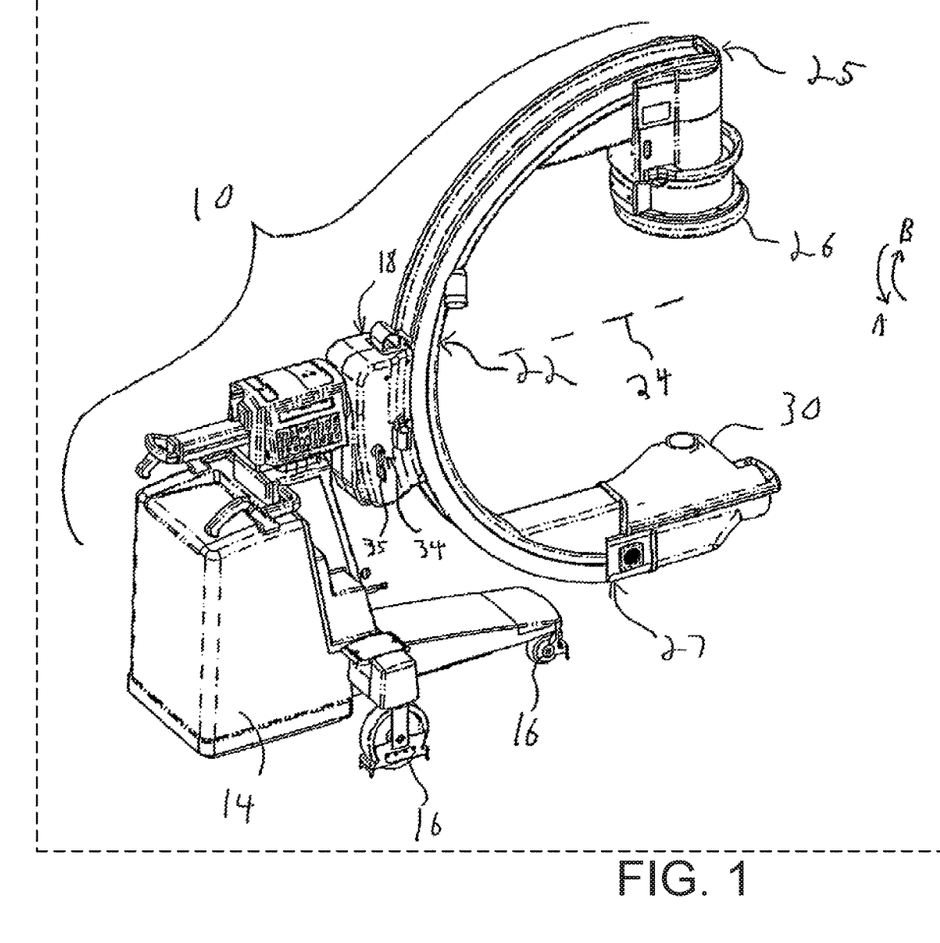
FIG. 1 depicts an isometric side view of a mobile imaging machine of a previous example.
Figure 7:
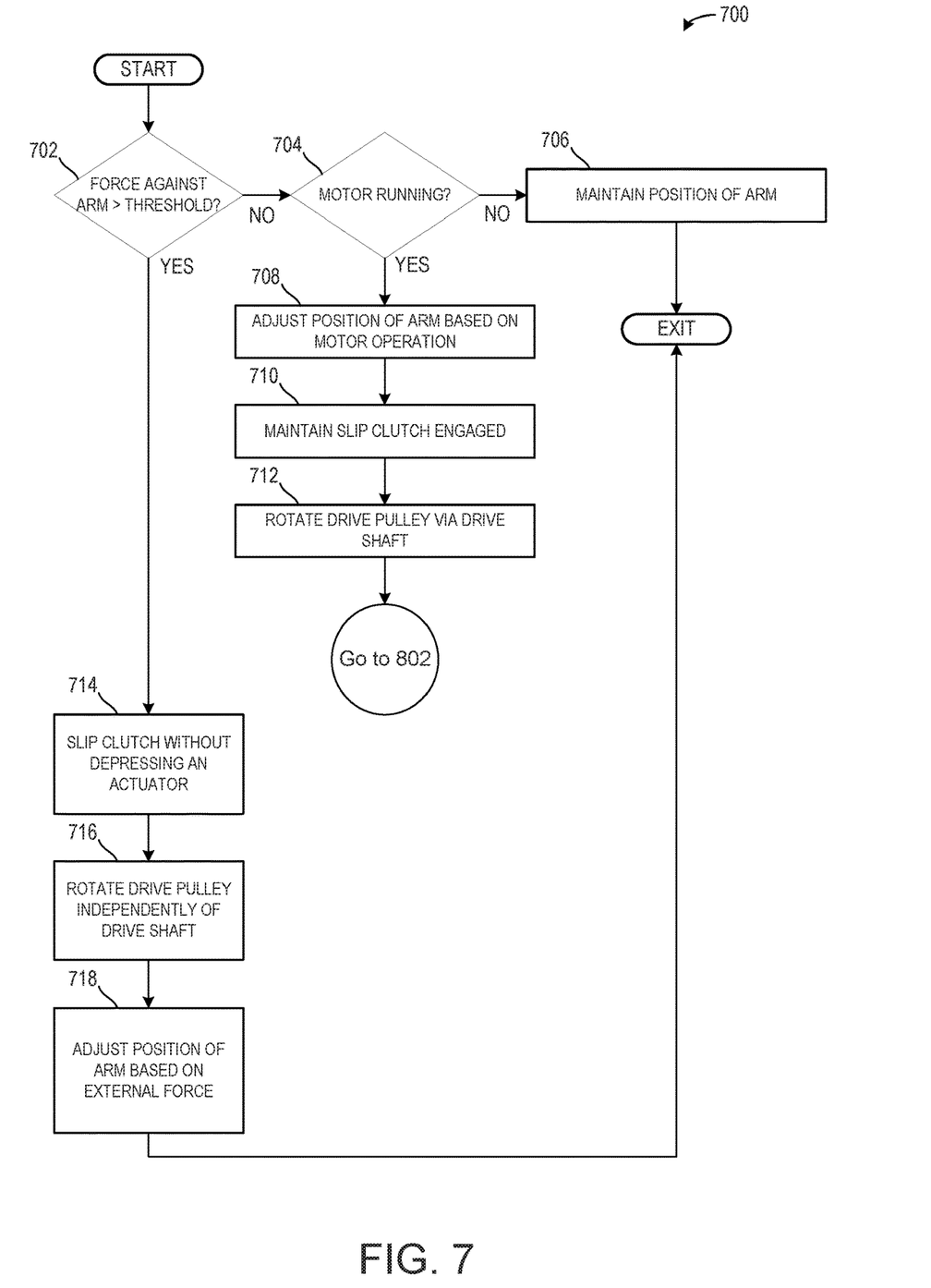
FIG. 7 shows a method for operating the drive assembly in response to a force applied to the arm.
Figure 8:
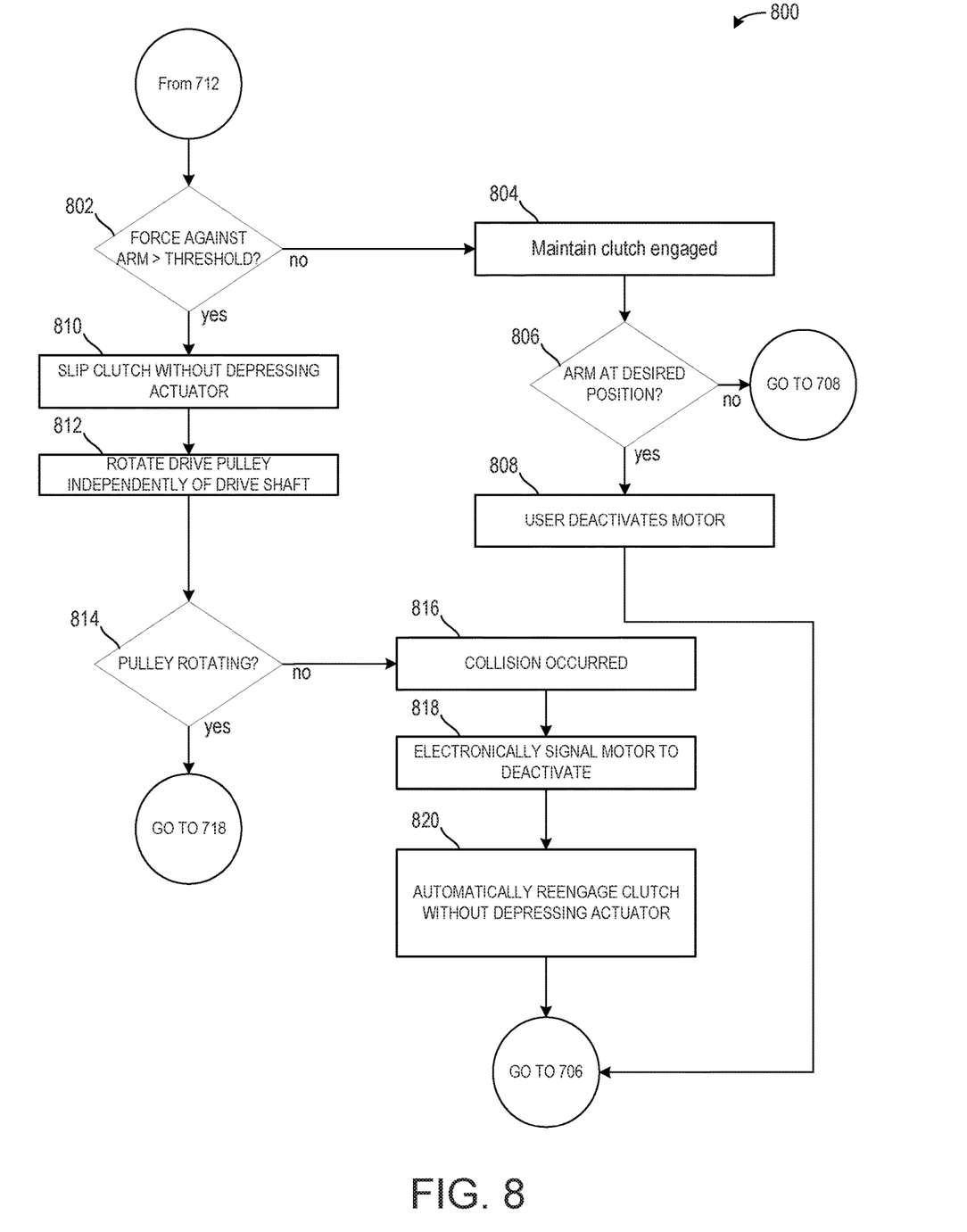
FIG. 8 shows a method for distinguishing between a collision and a user applied force during motorized movement of the arm.

The following description relates to embodiments of an X-ray system positioning device. A gantry and/or an imaging assembly of a mobile imaging system may include an imaging assembly comprising an arm, which may be moved during an imaging session via a motor or a user. FIG. 1 illustrates an embodiment of the X-ray system positioning device comprising a C-arm. In one example of the present disclosure, a drive assembly of the gantry comprises a clutch mechanism configured to allow the mobile imaging system to switch between adjusting a position of an arm of the gantry via a drive train or manually via a user in response to a force applied to the arm. Various views of the arm and the drive train and its components are illustrated in FIGS. 2A through 6B. A method for adjusting operation of the drive train in response to a force against the arm of the imaging assembly is shown in FIG. 7. A method for distinguishing between a force due to a collision and a user applied force during a motorized operation of the arm is illustrated in FIG. 8.

The arm may be a support arm that extends between an X-ray source and an X-ray detector positioned opposite one another. The support arm may allow the imaging assembly to move with respect to the main assembly. The drive train of the arm comprises the clutch mechanism configured to slip in response to a force applied to the arm. If the force exceeds a threshold force, then the clutch may slip and the drive pulley may be decoupled from the drive train, allowing the drive pulley to rotate independently of the drive train. This may provide some advantages relative to previous examples of an X-ray positioning device. In one example, scan times may be faster as an actuator is no longer engaged/disengaged to enable manual movement of the arm and disengage the motor. In this way, the switching between adjusting the position of the arm via the drive train or the user is in response to only the force applied to the arm and not to an electrical signal or depression and/or of a button, a lever, or other similar device. In one example, this configuration may be beneficial during a procedure in which a medical emergency occurs as a physician may quickly move the arm with a single force against the arm. Additionally, the clutch may slip in response to colliding with an object, wherein oscillations and impact forces experienced by the drive train and other components of the arm may be reduced via the clutch slipping. As such, a longevity of the arm and its drive train may be increased relative to the previous examples.

FIGS. 1 to 6B show example configurations with relative positions of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space therebetween and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example.

FIG. 1 is an isometric side view of a previous example of a mobile imaging machine 10. The imaging machine 10 includes a mobile support structure 14, a carrier 18, and a curved positioning arm 22 (which is illustrated as a C-arm). Although the curved arm 22 is illustrated as a C-arm, it will be appreciated that the arm 22 can have different shapes. For example, the arm 22 may be spiral in shape. The mobile support structure 14 has wheels 16, which allow the entire imaging machine 10 to be moved. The C-arm 22 is semi-circular in shape and carries an imaging receiver 26 at a first distal end 25 and an imaging source 30 at a second distal end 27. By way of example and not limitation, the imaging source 30 may be an x-ray source. A partially covered drive system or drive train 34 is mounted to the carrier 18. A wedge-shaped clutch handle 35 extends from the covered drive train 34 and is spring loaded to remain in an engaged position.

An operator may activate the drive train 34 by pressing a button or switch connected to the drive train 34 such that the drive train 34 engages the belt 42 in order to orbitally rotate the C-arm 22 along the carrier 18 in the direction of either arrow A or B. Alternatively, the drive train 34 may be electrically connected to an electronic controlling device, such as controller, comprising a joystick so that the operator can control the movement of the C-arm 22 with the joystick.

In operation, an operator may roll the mobile C-arm imaging machine 10 proximate a patient that is to be imaged. The operator positions the C-arm 22 in order that the patient is situated between the imaging source 30 and the imaging receiver 26. The operator may take an image (or series of images) of the patient and then move the C-arm 22 away from the patient. In order to position the C-arm 22 about the patient, the operator may rotate the C-arm 22 about the longitudinal axis 24 of a rotational knuckle to position the C-arm 22 about the patient. Additionally, the operator may activate the drive train 34 such that the drive train 34 engages the belt 42 (FIG. 7) in order to orbitally rotate the C-arm 22 along the carrier 18 in the direction of either arrow A or B.

Manipulating the C-arm 22 by use of the drive train 34 is the default method of orbitally rotating the C-arm 22. The operator may manually override this default method by rotating the clutch handle 35 clockwise from the engaged state to a disengaged state in order to disengage the drive train 34 from the belt 42. When the clutch handle 35 is in the release position, the operator may then manually manipulate the C-arm 22 to orbitally rotate the C-arm 22 about the carrier 18. Because the clutch handle 35 is spring loaded, the operator maintains the clutch handle 35 in the disengaged position in order to manually rotate the C-arm. When the operator has finished manually rotating the C-arm, the operator releases the clutch handle 35 from the disengaged position and the clutch handle 35 returns to the engaged position. The operator orbitally rotates the C-arm 22 in order to position the C-arm 22 about the patient such that the patient is situated between the imaging source 26 and imaging receiver 30. The operator may take an image of the patient and then move the C-arm 22 away from the patient.

Thus, in the previous example illustrated in FIG. 1, the operator (e.g., a user) is forced to depress an actuator to manual operate the C-arm 22. More specifically, the operator maintains the clutch in the disengaged position by rotating the clutch and blocking the clutch from rotating back to the engaged position. By doing this, the operator may use their hand free of the clutch to operate the C-arm 22.

The inventors have realized some issues with the system of FIG. 1. For example, imaging machines similar to the imaging machine 10 of FIG. 1 may be used during medical procedures where the operator may be performing a medical task (e.g., surgery). The operator (e.g. surgeon) may use both hands to perform a medical task and is situated beside the patient, away from the actuators, therefore they may not be able to rotate the clutch to a disengaged state or actuate some other actuator to switch the imaging machine from a motorized mode to a manual mode. Furthermore, if a patient is bleeding (e.g., hemorrhaging), the operator may need to move the arm quickly, wherein depression of the button or other actuator may delay treatment of the bleed.

As will be described herein with respect to FIGS. 2A through 8, an embodiment of a mobile imaging comprises an arm configured to be positioned manually or via a motor of an orbital drive mechanism. The arm may no longer be moved via the motor in response to a force applied to the arm. In one example, the force is greater than a threshold force set within a clutch mechanism of a drive train. The clutch mechanism is configured to slip and allow the drive pulley to rotate independently of a drive shaft in response to only a force exerted against the arm exceeding a threshold force.

In response to an absence of the force against the arm, the motor is configured to move the arm. As such, the clutch mechanism may remain engaged (e.g., not slip) and the arm may be moved via the drive shaft.

In one example, the arm may be moved via a drive train or via a force applied directly to the arm. The drive train is described in greater detail below with respect to FIGS. 2A-6B. The drive train comprises a clutch mechanism configured to slip automatically in response to only a force applied to the arm exceeding a threshold force. In one example, the desired threshold force may be adjusted and set on the clutch by adjusting the spring force of the clutch springs. In one example, the lowest threshold force may be set to a value greater than or equal to the force generated by the weight of the arm allowing the arm to maintain a stationary position without the need for additional braking forces or components. Setting the clutch at the minimum threshold force provides a desired amount of stability to the arm while minimizing the force the user uses to exert on the arm to manually actuate the arm. In one example, if the user switches to manual operation, the push force needed to be greater than or equal to threshold force may be equal to a minimum value. Setting the threshold force at the minimum value will allow the user to switch to manual operation more quickly and easily. In an example where the arm collides with an object during motorized, a clutch configured at the minimum force will minimize the impact force of the collision.

Figure 2A:
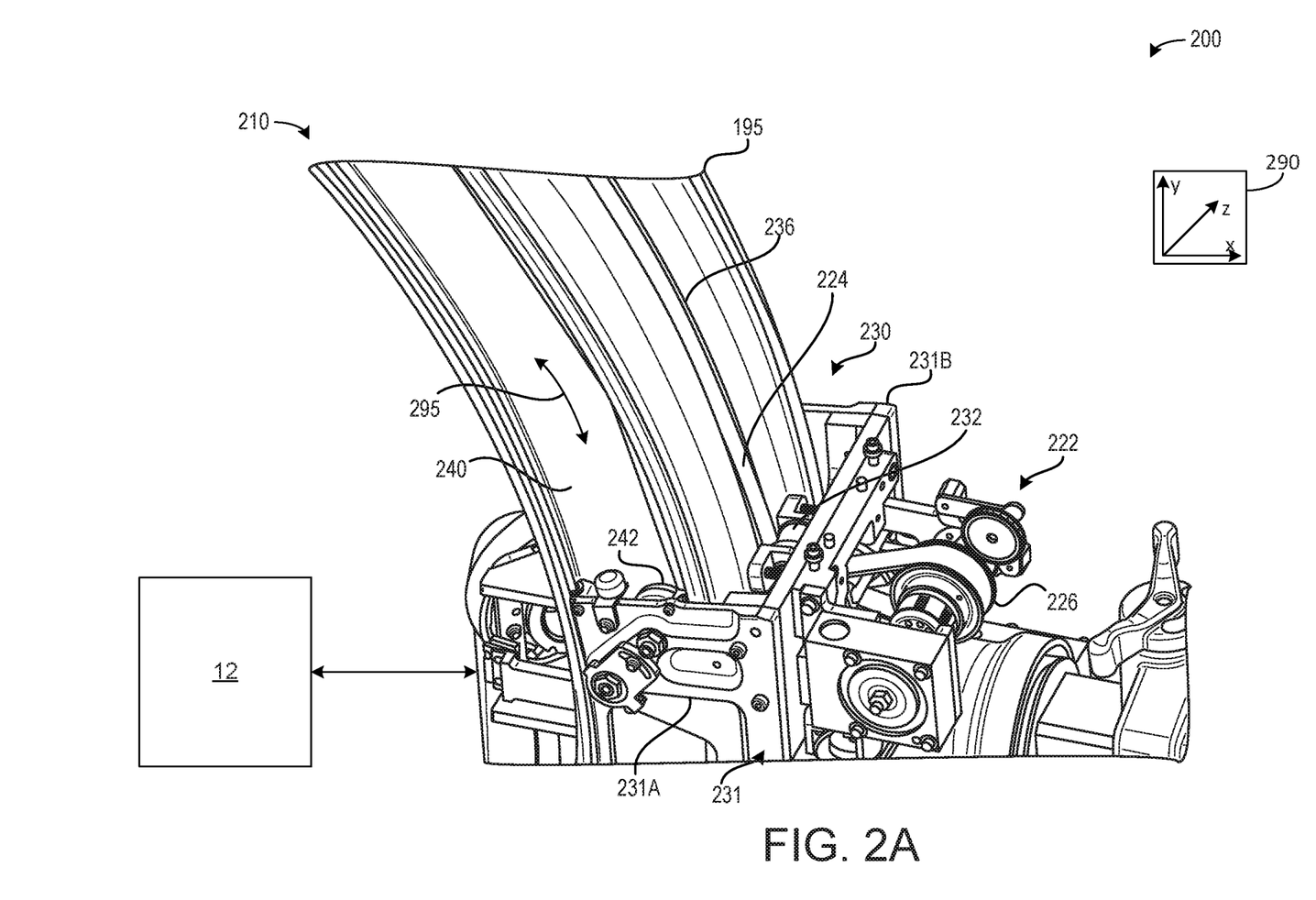
FIG. 2A shows a drive assembly mounted on a back of a carrier of an x-ray machine.
Figure 2B:
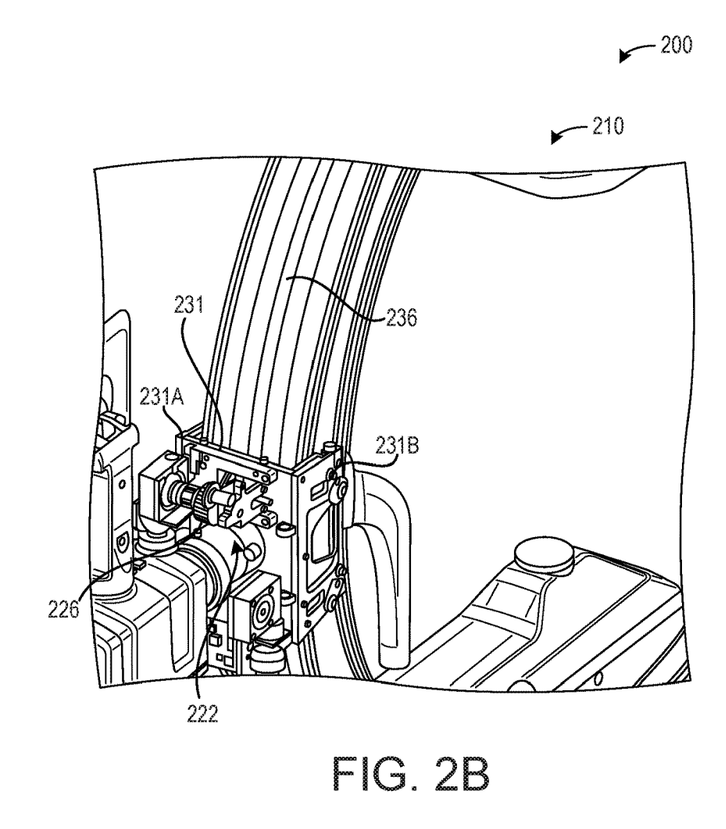
FIG. 2B shows an additional view of the drive assembly mounted on a back of a carrier of an x-ray machine.
Figure 2C:
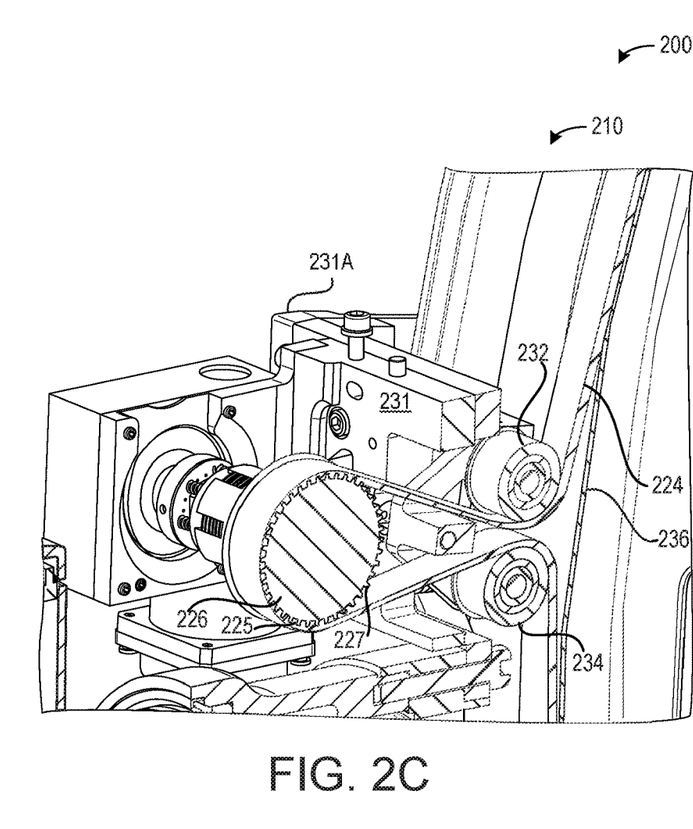
FIG. 2C shows a section view of the drive assembly mounted on a back of a carrier of an x-ray machine.

Turning now to FIGS. 2A, 2B, and 2C, they show an embodiment 200 of an orbital drive mechanism 222 configured to move an arm 195 of an imaging system 210. As such, components may be similarly numbered in this figure and subsequent figures. An axis system 290 is shown comprising three-axes, namely an x-axis parallel to a horizontal direction, a y-axis parallel to a vertical direction, and z-axis perpendicular to the x- and y-axes. In one example, the axis about which the orbital drive mechanism moves the arm 195 is parallel to the z-axis.

The orbital drive mechanism 222 may be arranged at a back side 230 of the arm 195, between the arm 195 and a wheeled structure. In one example, a carrier 231 may be arranged between the orbital drive mechanism 222 and the arm 195. The carrier 231 may mount the orbital drive mechanism 222 to the arm 195. The carrier 231 may comprise first and second brackets 231A, 231B engaged with the arm 195, wherein the brackets may comprise features that enable the arm 195 to move between the brackets. In one example, the first bracket 231A is identical to the second bracket 231B. The carrier 231 may remain stationary as the arm 195 is moved relatively thereto.

The orbital drive mechanism 222 may move the arm 195 via a belt 224. As shown in FIGS. 2B and 2C, the drive pulley 226 may comprise teeth 227 for engaging with teeth 225 of the belt 224. As such, a shape of the teeth 225 and teeth 227 may be complementary to one another such that a tooth of the teeth 225 fits between adjacent teeth of the teeth 227. The belt 224 may be in face-sharing contact with greater than half of a surface of the drive pulley 226. A pair of rollers, including a first roller 232 and a second roller 234 maintain a position of the belt 224 as opposite ends of the belt 224 extend toward opposite ends of the arm 195. Additionally or alternatively, the first roller 232 and the second roller 234 may maintain a tension of the belt 224 such that the tension does not decrease or increase. In one example, a first extreme end of the arm 195 comprises an X-ray source (e.g., X-ray source 610 of FIG. 6A) and a second extreme end, opposite the first extreme end of the arm 195, comprises an X-ray detector (e.g., detector 605 of FIG. 6A). The belt 224 may be situated along a recess 236 arranged on the back side 230 (e.g., a non-imaging side) of the arm. In one example, the orbital drive mechanism 222 is mounted to the arm 195 such that a middle of the belt 224 is engaged with the drive pulley 226. However, during some positions of the arm 195, it will be appreciated that other portions of the belt 224 may be engaged with the drive pulley 226.

When the belt 224 is moved, the arm, including the X-ray source and X-ray detector, may be repositioned while remaining directly opposite one another via a movement of the entire arm 195. As will be described herein, the orbital drive mechanism 222 may comprise a motor and a clutch mechanism, wherein the orbital drive mechanism 222 may be configured to move the arm 195 via its motor during some conditions. During other conditions, the arm 195 may be configured to move via an outside force without input from the motor. That is to say, during some conditions, the outside force may be provided by a user or foreign object, wherein motion of the arm 195 is no longer provided via the motor of the orbital drive mechanism 222.

Actuating the belt 224 may result in rollers 242 of the first bracket 231A arranged in a side rail 240 of the arm 195 to rotate as the arm 195 moves along the direction of double headed arrow 295. The arm 195 may further comprise a side rail corresponding to the second bracket 231B, wherein a roller of the second bracket 231B may rotate within its corresponding side rail. In some embodiments, multiple rollers may be arranged in each bracket.

Figures 3A, 3B:
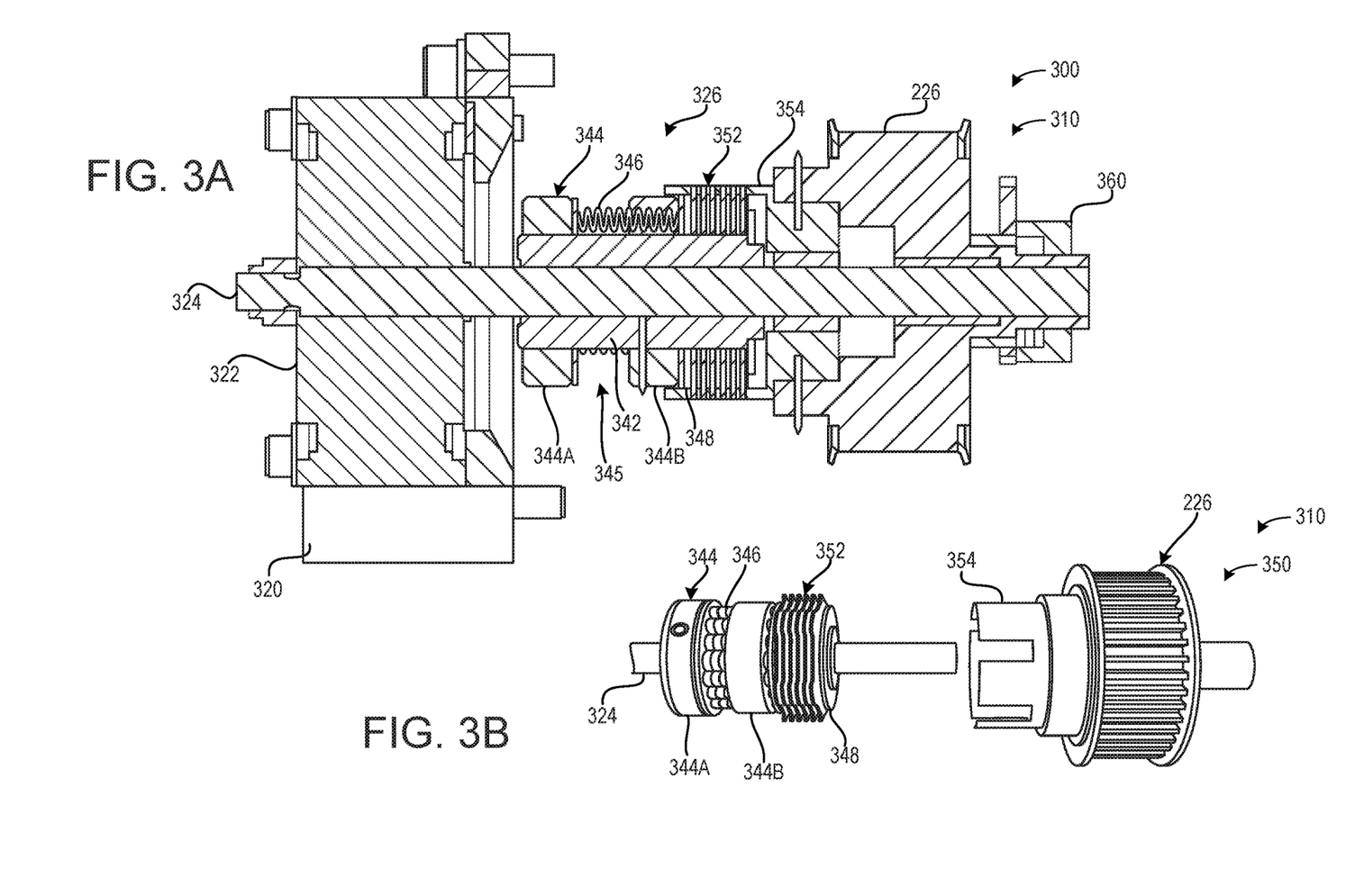
FIG. 3A shows a section view of the drive assembly.
FIG. 3B shows a perspective view of a portion of the drive assembly

Turning now to FIGS. 3A and 3B, they show embodiments 300 and 350, respectively, of a drive assembly 310, which may be a non-limiting example of the orbital drive mechanism 222 of FIGS. 2A, 2B, and 2C. Embodiment 300 of FIG. 3A illustrates a cross-section of the drive assembly 310 and embodiment 350 of FIG. 3B illustrates a perspective view of a portion of the drive assembly 310.

The drive assembly 310 comprises a motor 320, a gearbox 322, a drive shaft 324, a clutch mechanism 326, and the drive pulley 226. The gearbox 322 may be operated in combination with the motor 320 to transfer power from the motor 320 to the drive shaft 324. In this way, the motor 320 may rotate one or more gears with in the gearbox 322, which may result in rotation of the drive shaft 324. The gearbox 322 is locked to an end of the drive shaft 324, in one example.

The clutch mechanism 326 may comprise a clutch shaft 342 fixedly coupled to the drive shaft 324. In one example, the clutch mechanism 326 is a slip clutch. In one example, a plurality of setscrews may be used to physically couple the clutch shaft 342 to the drive shaft 324. A clutch cartridge 344, may be physically coupled to the clutch shaft 342 via one or more fastening devices. The physical coupling may be an example of a rotatable coupling such that the clutch shaft 342 rotates with the drive shaft 324 while being coupled to the clutch cartridge 344.

In one example, the clutch cartridge 344 comprises two portions, a first portion 344A adjacent to the gearbox 322 and a second portion 344B distal to the gearbox 322. One or more springs 346 may extend from the first portion 344A or the second portion 344B to a plurality of pressure plates 348. In one example, the springs may be arranged between first portions of the clutch mechanism. For example, the springs 346 may be arranged between the drive shaft and the clutch shaft and the pressure plates. In one example, a gap 345 is arranged between the first portion 344A and the second portion 344B of the clutch cartridge 344, wherein the one or more springs 346 completely traverse the gap 345, from an extreme end of the first portion 344A distal to the gearbox 322, to an end of the plurality of pressure plates 348 interfacing with the second portion 344B. The one or more springs 346 may press against the pressure plates 348. In one example, the one or more springs 346 press against the one or more of the plurality of pressure plates 348 in response to a rotation of the drive shaft 324.

In one example, the first portion 344A is an adjustment collar. Additionally or alternatively, the first portion 344A may be omitted in some examples of the clutch mechanism.

A plurality of boss capture arms 352 may be coupled to the plurality of pressure plates 348 and to a clutch boss 354. In one example, the plurality of boss capture arms 352 are fixedly coupled to the clutch boss 354. Furthermore, the plurality of boss capture arms 352 may remain fixedly coupled to the clutch boss 354 during all operating conditions, in one example. When the plurality of boss capture arms 352 rotate, the clutch boss 354 may also be rotated. The clutch boss 354 may be physically coupled to the drive pulley 226 such that rotation of the clutch boss 354 may result in rotation of the drive pulley 226. In some examples, additionally or alternatively, the clutch boss 354 and the drive pulley 226 may be integrally shaped into a single component. As described above, the rotation of the drive pulley 226 may result in the adjustment of the arm 195 of the X-ray device. As eluded to above, a force acting against the arm 195 may result in the clutch boss 354 and the drive pulley 226 freely rotating about the drive shaft 324 such that the force applied to the arm does not apply a counterforce to the drive shaft 324 or to the motor 320. As such, a longevity of the drive assembly 310 may be improved due to an absence of the counterforce which may mitigate backlash in the gearbox and motor. Additionally, the clutch boss 354 and the drive pulley 226 may freely rotate automatically via the configuration of the drive assembly 310 and the clutch mechanism 326. That is to say, automatically allowing the clutch boss 354 and the drive pulley 226 to freely rotate may include where a button or other similarly actuator is not depressed to switch from motor operation of the drive pulley 226 to manual operation of the drive pulley 226, wherein the manual operation comprises applying a force to the arm 195 in the orbital direction, which in turn applies a torque to the pulley and clutch boss via the belt. The torque on the clutch boss is transferred to the boss capture arms via the fixedly coupled connection between the two components. The boss capture arms resist the torque applied by the clutch boss and remain stationary via the resistive force between the pressure plates. In response to the torque exceeding the resistive threshold force between the pressure plates, the capture arms begin to rotate around the clutch shaft allowing the clutch boss and drive pulley to also rotate. Rotation of the capture arms is the mechanism by which the drive pulley is decoupled from the drive shaft allowing orbital rotation of the arm 195 independent of the motor. In this way, the user applied force on the arm or other portions of the imaging assembly automatically switches the arm 195 positioning method from motorized operation to a manual operation. In this same way, the normal force exerted by on object on the imaging assembly or arm 195 due to a collision will also cause the clutch to slip. The same resistive force between the pressure plates is what keeps the imaging assembly in a stationary position when neither manual or motorized operation is being used.

Specifically, in FIG. 3B, it shows the drive pulley 226 and the clutch boss 354 separately from the remaining portion of the drive assembly 310, wherein the remaining portion includes the motor 320, the gearbox 322, the drive shaft 324, the clutch mechanism 326, the one or more springs 346, and the one or more boss capture arms 352. In one example, when a user applies a force against the arm, if the force exceeds the threshold force, then the drive pulley 226 and the clutch boss 354 may rotate based on the force applied to the arm and not based on a rotation of the drive shaft 324. However, in the absence of the force or when the force does not exceed the threshold force, then rotation of the drive pulley 226 may be only based on rotation of the drive shaft 324. In another example, the force may be generated in response to the arm colliding with a stationary object such that the force directs the arm to stop movement in its original direction. If the force exceeds the threshold force, then the clutch mechanism 326 may slip, allowing the drive pulley 226 and the clutch boss 354 to stop rotating independently of the drive shaft 324. By doing this, degradation to the motor 320 due to collision may be mitigated.

In one example, a threshold force of the drive assembly 310 is set based on a tension of the one or more springs 346. The configuration allows the threshold force to be selected from a large range of values and the chosen threshold may be set on the clutch based on a plurality of conditions including a balance and/or a stability of the arm and an ease of switching to a manual mode via applying a low force to the arm. That is to say, the selected threshold force decreases the less user applied force is needed to manually position the arm 195 and the easier to switch from motorized operation to manual operation The drive mechanism 310 is further illustrated comprising a sensor 360. The sensor 360 may be a sensor configured to detect a position of the arm based on a motion of the drive pulley 226. In one example, the sensor 360 is a first sensor, further comprising a second sensor (e.g., second sensor 362 of FIG. 4A) configured to detect an output of the motor 320. During some conditions, such as when a force against the arm is detected, outputs from the first sensor 360 and the second sensor 362 may be compared.

Figure 4A:
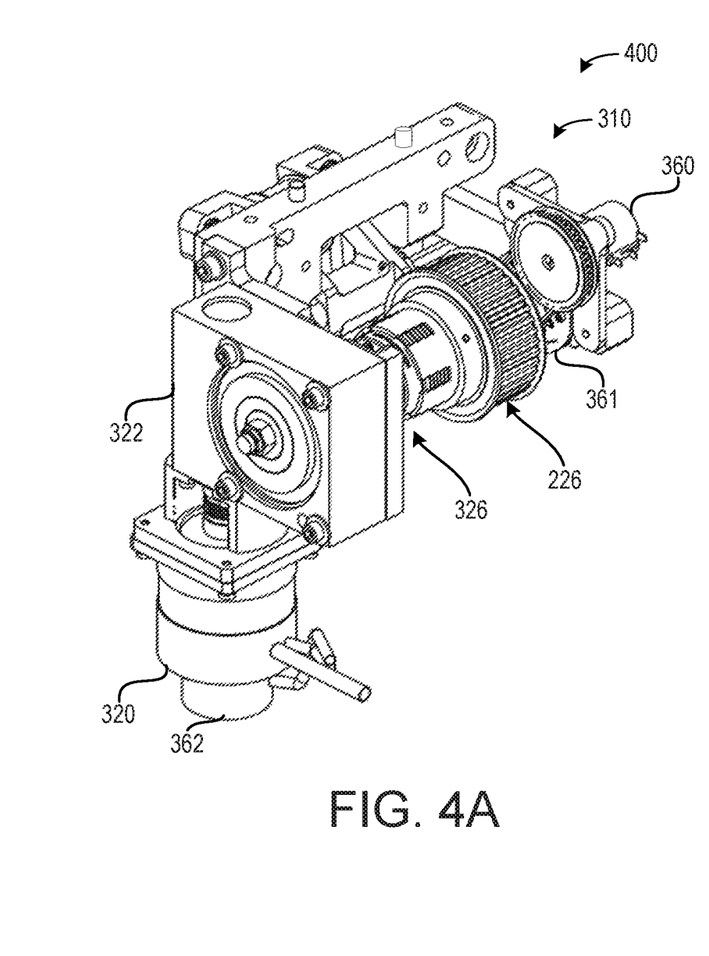
FIGS. 4A and 4B show perspective rear and front views of the drive assembly, respectively.
Figure 4B:
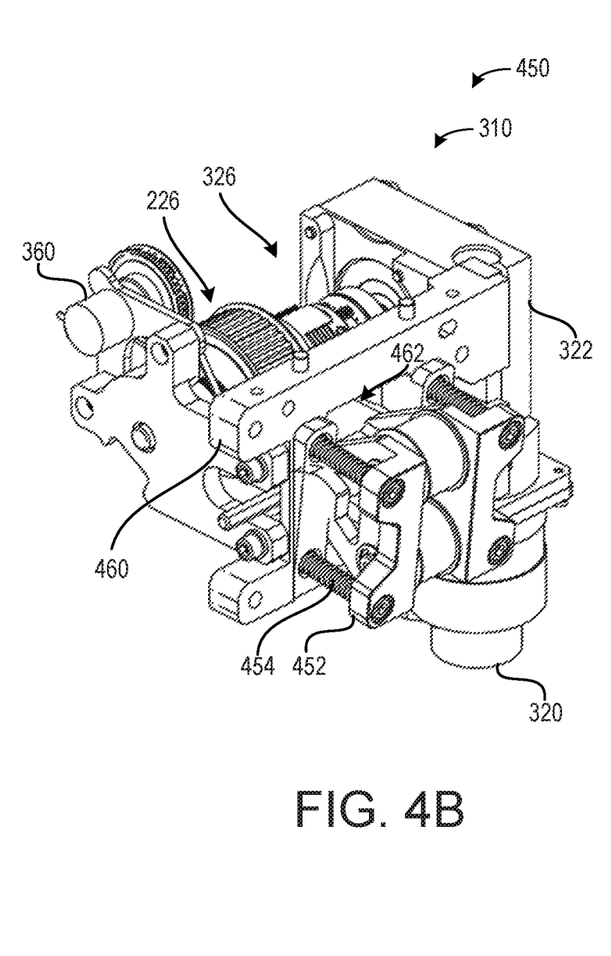
Figure 5A:
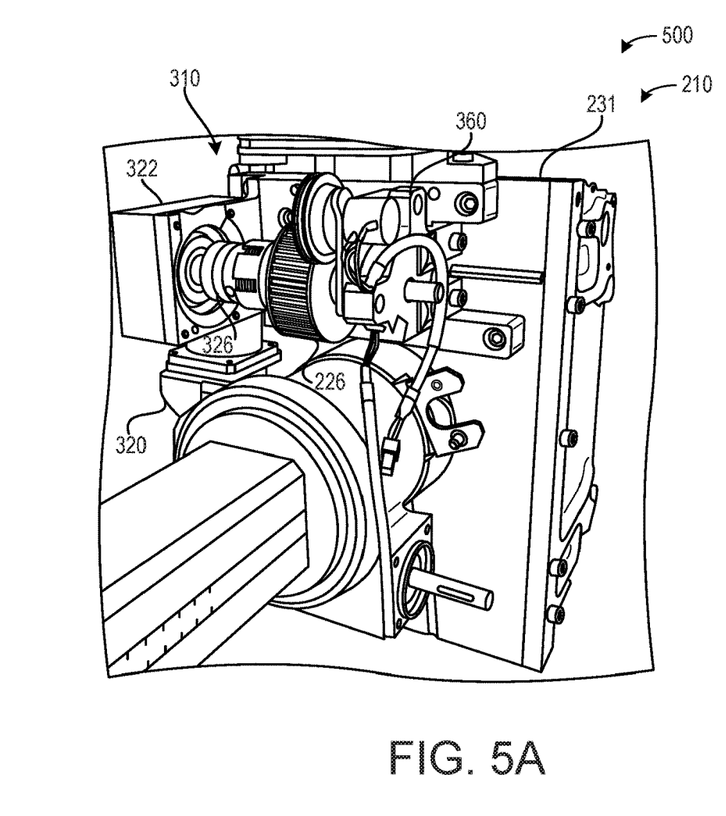
FIG. 5A shows a view of the drive assembly mounted to a back of a carrier.
Figure 5B:
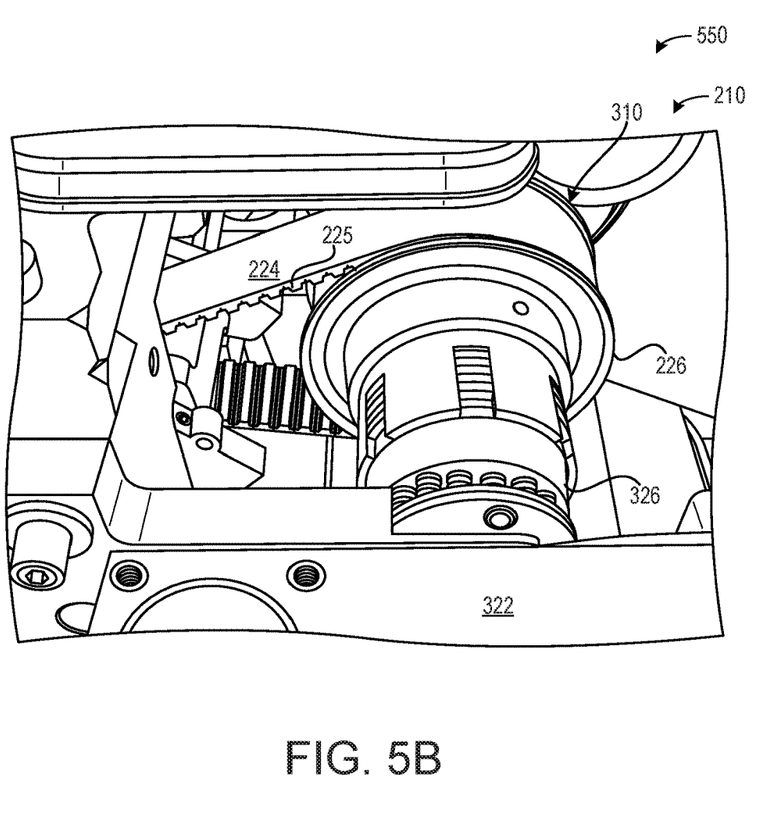
FIG. 5B shows a belt engaging with a drive pulley.

Turning to FIGS. 4A and 4B, they show a first view 400 and a second view 450 of the drive assembly 310, respectively. The first view 400 illustrates a back of the drive assembly 310 further away from an arm (e.g., the arm 195 of FIG. 2A) relative to a front of the drive assembly 310 illustrated in the second view 450. Each of the motor 320, the gearbox 322, the clutch mechanism 326, and the drive pulley 226 are exposed in the first view 400. The motion of the drive pulley 226 may be tracked via the first sensor 360 and a circuit 361 coupled to the first sensor 360, wherein each of the circuit 361 and the first sensor 360 may track motion of the drive pulley 226 via different mechanisms. In one example, the first sensor 360 tracks the drive pulley 226 via one or more magnets and the circuit 361 tracks the drive pulley 226 via a current. In the second view 450, the first roller 232, the second roller 234, and a frame 452 are shown. The frame 452 may be physically coupled to a body 460 of the drive assembly 310 via a plurality of couplings 454. The plurality of couplings 454 may include one or more bolts, welds, fusions, or the like. In the example of FIG. 4B, the plurality of couplings 454 include four fasteners, such as bolts. As described above, a belt may engage with the drive pulley 226 and extend through an opening 462 of the body 460, wherein the belt may contact surfaces of the first and second rollers 232, 234. In one example, the body 460 and the frame 452 may be components of the carrier (e.g., carrier 231 of FIG. 2A).

Figure 6A:
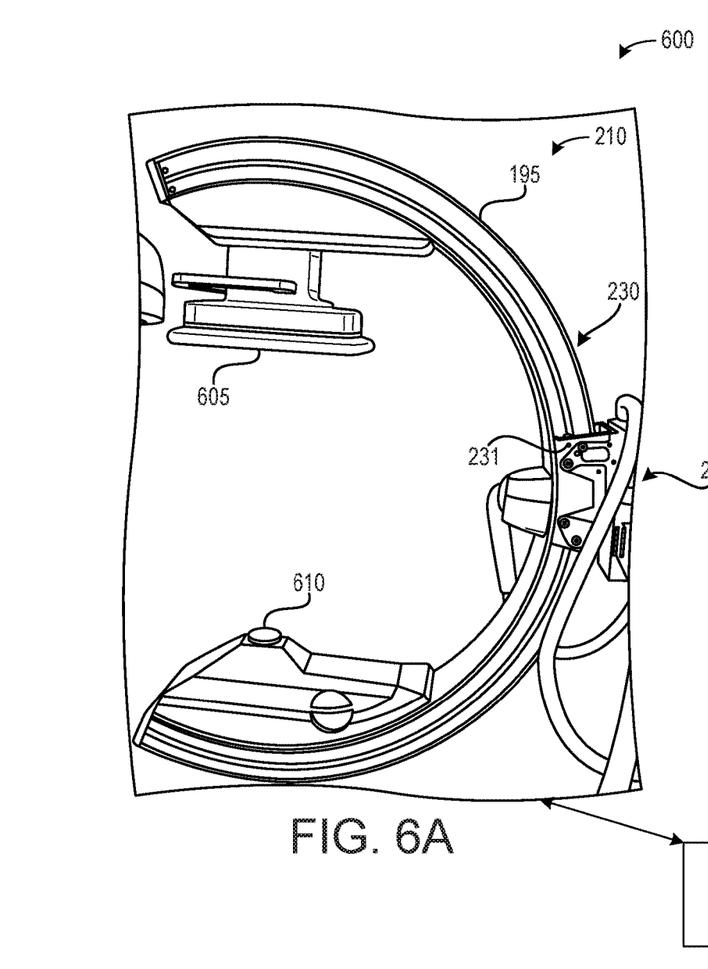
FIG. 6A shows an arm to which the drive assembly is coupled.
Figure 6B:
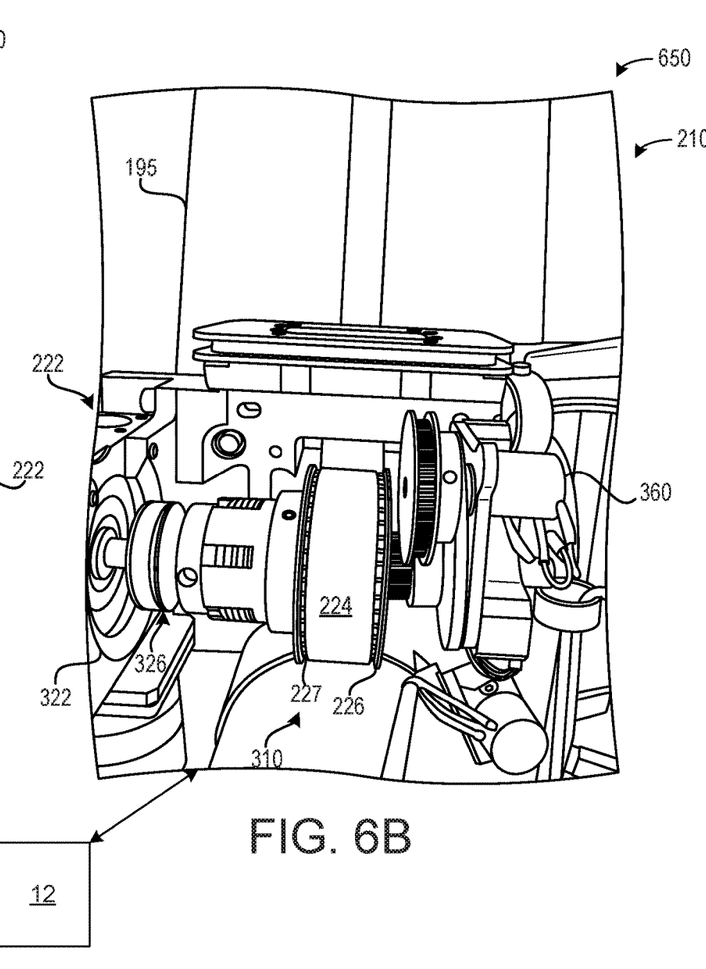
FIG. 6B shows the drive assembly coupled to a non-scanning side of the arm.

Turning now to FIGS. 5A, 5B, 6A, and 6B, they show various views 500, 550, 600, and 650, respectively, of the drive mechanism 310. View 500 illustrates the drive mechanism 310 coupled to the carrier 231 and view 600 illustrates the carrier 231 physically coupled to the back side 230 of the arm 195. View 550 illustrates teeth 225 of the belt 224. The belt 224 is shown engaged with the drive pulley 226 in view 650, wherein teeth 227 of the drive pulley 226 are exposed. The teeth 225 and 227 may engage with one another such that movement of the belt 224 may be more stable. The embodiments of FIGS. 5A through 6B illustrate one exemplary embodiment of the drive mechanism 310 coupled to the arm 195. FIG. 6A further illustrates an X-ray detector 605 arranged opposite to an X-ray source 610 on the C-arm 195. It will be appreciated that the x-ray detector 605 and the X-ray source 610 may remain opposite of one another through motorized and manual movement of the C-arm 195.

The imaging system 210 may comprise a controller 12, configured to receive information from a plurality of sensors (such as the first sensor 360 and the second sensor 362 of FIG. 4A). In one example, sensors may include sensors coupled to a drive train, wherein the sensors may monitor differences between rotation of a motor and rotation of a drive pulley included in the drive train. Additionally or alternatively, the controller 12 may receive feedback from the X-ray detector 605.

The controller 12 may further comprise non-transitory memory with instructions stored thereon that enable the controller 12 to learn a home scanning position and additional scanning positions of the arm 195 during a scanning procedure. The instructions may further enable the controller 12 to determine a deviation from a learned position due to manual operation of the arm 195. Additionally or alternatively, the instructions may enable the controller 12 to determine an interruption in a travel path from a first learned position to a second learned position due to a collision with an object during motorized movement of the arm.

In a real-world example, the imaging system 210 may be used during conditions where a mobility of an object (e.g., a patient) to be scanned is limited. As such, the arm 195 may be repositioned, manipulated, articulated, rotated, and/or positioned to one or more desired positions to acquire various scans at a variety of angles. Prior to acquisition of the scans, the user may select a scan type which may correspond to a region of the object and/or condition of the object. One or more scan positions and/or scan angles may be associated with the scan type, such that upon selection of the scan type, the arm 195 may be moved to the one or more scan positions. However, due to a disparity between objects and/or due to complications during a procedure being conducted in tandem with the scanning, the user may desire scans from positions other than those learned. As such, the user may move the arm with a force greater than the threshold force, in which case motorized operation of the arm is automatically disabled. In one example, the arm may return to motorized operation in response to an absence of a user applied force if imaging is still desired. Operation of the arm along with components of the drive train (e.g., a drive mechanism) are described in greater detail herein. In one example, the force is a user-applied force on the arm, which may include a pull-force, a push-force, and/or other similar force.

Turning now to FIG. 7, it shows a method 700 for adjusting operation of the clutch mechanism to allow manual or motorized movement of an arm of a medical imaging device. In one example, the method may be described in relation to components previously including the arm 195, the motor 320, the gearbox 322, the drive shaft 324, the clutch mechanism 326, the clutch boss 354, the belt 222, and the drive pulley 226.

In one example, instructions for carrying out method 700 and the rest of the methods included herein may be executed by a controller based on instructions stored on a memory of the controller and in conjunction with signals received from sensors of the imaging system, such as the sensors described above with reference to FIG. 4A and the controller with respect to FIG. 2A.

The method 700 begins at 702, which comprises determining if a force against the arm is greater than the threshold force. The force may be applied by a user or object. In one example, the force may correspond to the user trying to move the arm in one or more directions. As another example, if the arm contacts an external object, such as an operating table, assistant, or other object, the external object may apply a force against the arm, which may impede or alter its original movement path. The threshold force may be based on a force at which the clutch mechanism is configured to slip. The threshold force may be set to a relatively low force that the user may quickly adjust operation of the arm from a motorized movement to a manual movement.

If the force against the arm is not greater than the threshold force, then the method 700 proceeds to 704, which comprises determining if a motor is running. If the motor is not running, then the method 700 proceeds to 706, which includes maintaining a position of the arm and does not adjust a position of the arm.

If the motor is running, then the method 700 proceeds to 708, which includes adjusting a position of the arm based on an operation of the motor. In the example of the motor 320 described above which is arranged in an orbital drive assembly 310 with respect to FIGS. 2A to 6B, the motor 320 may rotate the drive pulley via a drive shaft, which may result in rotation of the arm about an axis.

The method 700 proceeds to 710, which comprises maintaining the clutch mechanism engaged. The clutch mechanism remains engaged, which results in the clutch boss rotating in response to rotation of the plurality of boss capture arms. The plurality of boss capture arms rotates via the clutch shaft, which rotates in response to a rotation of the drive shaft, causing the drive pulley to rotate and adjust the arm via the belt. Said another way, when the clutch mechanism is in the engaged state, the drive shaft is coupled to the drive pulley and rotation of the drive shaft results in rotation of the drive pulley.

The method 700 proceeds to 712, which includes rotating the drive pulley via the drive shaft. As such, rotation of the drive shaft is imparted to the clutch shaft, which is imparted to the clutch boss, wherein the clutch boss is physically coupled to the drive pulley. By rotating the drive pulley, a belt to which the drive pulley is engaged may adjust a position of the arm, resulting a different scan angle and/or scan position of the X-ray source and detector.

Returning to 702, if the force against the arm is greater than the threshold, then the method 700 proceeds to 714, which includes slipping (e.g., disengaging) the clutch mechanism without depressing an actuator. The actuator may include a button, a lever, a tab, a pedal, and/or another similar device. In one example, the X-ray system is free of a button, the lever, the tab, the pedal, and/or another similar device previously used to switch between motorized and manual operation of the arm. As such, if a user decides to enter manual operation of the arm, the user may only apply a force to the arm without executing any other task or relaying an electrical signal via a button. By doing this, efficiency may be increased and manual operation may be less complex. Furthermore, due to the nature in which mobile X-ray system are utilized, work flow of the user may be less or not interrupted at all. In one example, the mobile X-ray system is used during surgery, in which case, a surgeon may move the arm with one hand and perform a surgical task with their other free hand that previously may have been used to signal a desire to switch to manual movement of the arm. In one example, the mobile X-ray system is used during surgery, in which case an emergency situation occurs and the surgeon needs to quickly move the arm out of their workspace. For example, if a patient begins bleeding, the surgeon may reflexively press against the arm to move it from their workspace. As such, in the example of the present disclosure, the arm may respond to the force from the surgeon and move in the desired direction allowing the surgeon to quickly tend to the emergency.

The method 700 proceeds to 716, which includes rotating the drive pulley independently of the drive shaft. Said another way, the method includes not rotating the drive pulley via the drive shaft. Thus, the slipped state and/or the disengaged state comprises where the drive shaft is uncoupled from the drive pulley and rotation of the drive shaft does not result in rotation of the drive pulley. The drive pulley may rotate in response to the force applied to the arm freely of the drive shaft. In one example, the drive pulley may rotate and the drive shaft may be stationary during the manual mode. In such an example, the motor may be deactivated upon entering the manual mode.

The method 700 proceeds to 718, which includes adjusting a position of the arm based on the external force. In one example, adjusting the position includes actuating the arm in a position different than an original path of travel, wherein the original path of travel was powered by the motor. In another example, adjusting the position includes stopping the arm 195 in a fixed location as the arm 195 was traveling along the original path. In such an example, a collision between the arm and an object may have occurred.

Turning to FIG. 8, it shows a method 800 for determining if a force against the arm during a motorized movement of the arm is due to a collision or manual manipulation of the arm. Following 712, the method 800 proceeds to 802 to determine if a force is greater than a threshold force, similar to 702. If the force is not greater than the threshold force, then the method 800 proceeds to 804 and maintains the clutch mechanism engaged, as previously described.

The method 800 proceeds to 806 to determine if the arm is at a desired position. In one example, a position sensor or other similar device may be used to determine a position of the arm. Additionally or alternatively, a camera or other imaging device may be used to determine a position of the arm relative to the patient. In some examples, the position of the arm may be estimated based on feedback from the first sensor and the second sensor in conjunction with data stored in a multi-input look-up table, wherein the inputs include drive pulley rotation and motor activation duration and at least one output includes an estimate of the arm position. If the arm is not in the desired position, then the method 800 proceeds to 708 as described above. If the arm is in the desired position, then the method 800 proceeds to 808 which comprises manually deactivating the motor. As such, a user may depress a button, flip a switch, or actuate some other actuator to deactivate the motor. In one example, the user does not apply a force to the arm to deactivate the motor. In some examples, in response to the arm reaching the desired position, an alert may be provided to the user, wherein the alert may include an audible noise and/or a message on a display screen.

Returning to 802, if the force is greater than the threshold force, then the method 800 proceeds to 810 which includes slipping the clutch mechanism without depressing the actuator, as described above at 714 of method 700. The method 800 proceeds to 812, which includes rotating the drive pulley independently of the drive shaft, as described above at 716 of method 700.

The method 800 proceeds to 814, which includes determining if the drive pulley is rotating. In one example, a sensor, such as the first sensor 360 of FIG. 4A, may detect a motion and/or a position of the arm based on a rotation of the drive pulley. If the motor is running (e.g. activated), which may be determined based on feedback from the second sensor 362 of FIG. 4A and the drive pulley is not rotating, then the method 800 may proceed to 816, which includes where a collision has occurred. As such, manual operation of the drive pulley is not occurring despite the force being greater than the threshold force.

The method 800 proceeds to 818, which comprises electronically signaling the motor to deactivate. In one example, the controller may signal to an actuator of the motor to deactivate the motor. As such, the motor may be shut-off and may no longer receive a power supply. In this way, the user does not deactivate the motor.

The method 800 proceeds to 820, which includes automatically reengaging the clutch mechanism without depressing an actuator. Additionally or alternatively, the controller may signal to activate the motor. Additionally or alternatively, a message may be displayed on a display device indicating to the user that an object is arranged along a travel path between a starting position and a desired final position. The user may provide an input as to when the object is displaced and the travel path is clear. The method 800 proceeds to 706.

Returning to 814, if the pulley is rotating, then the method 800 proceeds to 718 as described above and executes the manual operation of the arm.

Thus, in one aspect, a motorized arm of a medical imaging device may switch from a motorized operation to a manual operation in response to a force applied to the arm. The force may be imparted onto the arm via a user or an object. In the example of the user, the user may manually manipulate the arm with a force greater than a threshold force, thereby prompting a clutch mechanism to slip and allow the drive pulley to rotate freely of a drive shaft. Additionally or alternatively, if the arm collides with the object during the motorized manipulation of the arm, the motorized manipulation may automatically switch to the manual mode, similar to the switching in response to the user force, wherein the motor and the gearbox are uncoupled from the drive pulley. The uncoupling of the drive components at collision may minimize bouncing and other unwanted movements of the arm. The technical effect of automatically switching from a motorized manipulation of the arm to a manual manipulation of the arm is to decrease an impact force experienced by drive train components and the impacted object. Furthermore, the automatic switching may mitigate current overdraw from the motor at a time of the collision.

An embodiment of an imaging device, comprises a curved arm, a carrier that engages and supports the curved arm, wherein the curved arm is configured to move relative to the carrier, a belt extending through the carrier and traversing around a periphery of the curved arm, and a drive system comprising a motor, a drive shaft rotatably driven by the motor, a drive pulley coupled to the drive shaft via a clutch mechanism, wherein the drive pulley is configured to rotate and engage with the belt to move the curved arm without moving the carrier, wherein the clutch mechanism is configured to move between an engaged state and a disengaged state, wherein the engaged state comprises the driveshaft being rotatably coupled to the drive pulley and wherein the disengaged state comprises where the driveshaft is uncoupled from the drive pulley, and wherein the clutch mechanism is configured to switch between the engaged state and the disengaged state in response to a force applied to the curved arm.

A first example of the imaging device, further comprises where the drive pulley is configured to rotate via a rotation of the driveshaft when the clutch mechanism is in the engaged state.

A second example of the imaging device, optionally comprising the first example, further comprises where the drive pulley is configured to rotate via only the force applied to the curved arm when the clutch mechanism is disengaged.

A third example of the imaging device, optionally comprising one or more of the previous examples, further comprises where the clutch mechanism switches from the engaged state to the disengaged state in response to the force being greater than or equal to a threshold force, wherein the threshold force is based on a weight of the curved arm, wherein the weight allows the arm to maintain a stationary position without braking forces or components.

An example of an X-ray system, comprises a moveable arm comprising an X-ray source and an X-ray detector, wherein a drive mechanism of the moveable arm comprises a motor, a clutch mechanism, and a drive pulley, and wherein the clutch mechanism is configured to disengaged in response to a force applied to the moveable arm exceeding a threshold force.

A first example of the X-ray system, further comprises where the clutch mechanism is switched between its engaged and disengaged states without use of an electrical signal, button, a lever, a switch, a pedal, or an actuator A second example of the X-ray system, optionally comprising the first example, further comprises where the moveable arm is a curved arm.

A third example of the X-ray system, optionally comprising one or more of the previous examples, further comprises where the drive mechanism is an orbital drive mechanism.

A fourth example of the X-ray system, optionally comprising one or more of the previous examples, further comprises where the moveable arm is one of a C-arm, or an O-arm.

A fifth example of the X-ray system, optionally comprising one or more of the previous examples, further comprises where a drive shaft rotatably coupled to a gearbox, the gearbox coupled to the motor, wherein the drive shaft rotates independently of the drive pulley when the clutch mechanism is disengaged.

A sixth example of the X-ray system, optionally comprising one or more of the previous examples, further comprises where the drive pulley rotates or remains stationary in response to the force exceeding the threshold force.

A seventh example of the X-ray system, optionally comprising one or more of the previous examples, further comprises where the threshold force is set via a spring tension of a spring of the clutch mechanism, wherein the spring presses against a one or more of pressure plates.

An embodiment of a system, comprises a mobile X-ray device comprising a C-arm, a drive mechanism configured to move the C-arm via a motor when a clutch mechanism is in an engaged state, wherein the clutch mechanism is configured to move to a disengaged state only in response to a force against the C-arm, and a controller with computer-readable instructions stored on non-transitory memory thereof that when executed enable the controller to during movement of the C-arm via the motor, determining a motion of a drive pulley in response to the force against the C-arm exceeding a threshold force and the clutch mechanism being in the disengaged state.

A first example of the system further includes where the instructions further enable the controller to determine a collision has occurred in response to the drive pulley being stationary, wherein the controller signals the motor to deactivate, wherein clutch mechanism is returned to the engaged state.

A second example of the system, optionally including the first example, further includes where the instructions further enable the controller to determine a manual operation of the C-arm is occurring in response to the drive pulley moving.

A third example of the system, optionally including one or more of the previous examples, further includes where the drive pulley is engagingly coupled to a belt via a plurality of teeth, and wherein the belt extends to opposite ends of the C-arm.

A fourth example of the system, optionally including one or more of the previous examples, further includes where a first portion of the arm comprises an X-ray source and a second portion of the C-arm, opposite the first portion, comprises an X-ray detector.

A fifth example of the system, optionally including one or more of the previous examples, further includes where the engaged state comprises where a drive shaft is coupled to the drive pulley.

A sixth example of the system, optionally including one or more of the previous examples, further includes where the disengaged state comprises where a drive shaft is uncoupled from the drive pulley.

A seventh example of the system, optionally including one or more of the previous examples, further includes where the clutch mechanism comprises a spring or plurality of springs pressing against a pressure plate or plurality of pressure plates As used herein, an element or step recited in the singular and proceeded with the word "a" or "an" should be understood as not excluding plural of said elements or steps, unless such exclusion is explicitly stated. Furthermore, references to "one embodiment" of the invention do not exclude the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

The control methods and routines disclosed herein may be stored as executable instructions in non-transitory memory and may be carried out by the control system including the controller in combination with the various sensors, actuators, and other hardware. The specific routines described herein may represent one or more of any number of processing strategies such as event-driven, interrupt-driven, multi-tasking, multi-threading, and the like. As such, various actions, operations, and/or functions illustrated may be performed in the sequence illustrated, in parallel, or in some cases omitted. Likewise, the order of processing is not necessarily required to achieve the features and advantages of the example embodiments described herein, but is provided for ease of illustration and description. One or more of the illustrated actions, operations and/or functions may be repeatedly performed depending on the particular strategy being used. Further, the described actions, operations and/or functions may graphically represent code to be programmed into non-transitory memory of the computer readable storage medium in the control system, where the described actions are carried out by executing the instructions in a system including the various hardware components in combination with the electronic controller.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. An imaging device, comprising:
a curved arm;

a carrier that engages and supports the curved arm, wherein the curved arm is configured to move relative to the carrier;

a belt extending through the carrier and traversing around a periphery of the curved arm; and a drive system comprising a motor;

a drive shaft rotatably driven by the motor;

a drive pulley coupled to the drive shaft via a slip clutch mechanism, wherein the drive pulley is configured to rotate and engage with the belt to move the curved arm without moving the carrier, wherein the slip clutch mechanism is configured to move between an engaged state and a disengaged state, wherein the engaged state comprises the driveshaft being rotatably coupled to the drive pulley and wherein the disengaged state comprises where the driveshaft is uncoupled from the drive pulley, and wherein the slip clutch mechanism is configured to switch between the engaged state and the disengaged state in response to a force applied to the curved arm.

2. The imaging device of claim 1, wherein the drive pulley is configured to rotate via a rotation of the driveshaft when the slip clutch mechanism is in the engaged state.

3. The imaging device of claim 1, wherein the drive pulley is configured to rotate via only the force applied to the curved arm when the slip clutch mechanism is disengaged.

4. The imaging device of claim 1, wherein the slip clutch mechanism switches from the engaged state to the disengaged state in response to the force being greater than or equal to a threshold force, wherein the threshold force is based on a weight of the curved arm, wherein the weight allows the arm to maintain a stationary position without braking forces or components.

5. An X-ray system, comprising:

a moveable arm comprising an X-ray source and an X-ray detector, wherein a drive mechanism of the moveable arm comprises a motor, the slip clutch mechanism, and a drive pulley, and wherein the slip clutch mechanism is configured to disengaged in response to a force applied to the moveable arm exceeding a threshold force, and wherein the slip clutch mechanism is switched between its engaged and disengaged states without use of an electrical signal, button, a lever, a switch, a pedal, or an actuator.

6. The X-ray system of claim 5, wherein the moveable arm is a curved arm.

7. The X-ray system of claim 5, wherein the drive mechanism is an orbital drive mechanism.

8. The X-ray system of claim 5, wherein the moveable arm is one of a C-arm, or an O-arm.

9. The X-ray system of claim 5, further comprising a drive shaft rotatably coupled to a gearbox, the gearbox coupled to the motor, wherein the drive shaft rotates independently of the drive pulley when the slip clutch mechanism is disengaged.

10. The X-ray system of claim 5, wherein the drive pulley rotates or remains stationary in response to the force exceeding the threshold force.

11. The X-ray system of claim 10, wherein the threshold force is set via a spring tension of a spring of the slip clutch mechanism, wherein the spring presses against a one or more of pressure plates.

12. A system, comprising:

a mobile X-ray device comprising a C-arm;

a drive mechanism configured to move the C-arm via a motor when the slip clutch mechanism is in an engaged state, wherein the slip clutch mechanism is configured to move to a disengaged state only in response to a force against the C-arm; and a controller with computer-readable instructions stored on non-transitory memory thereof that when executed enable the controller to:

during movement of the C-arm via the motor, determining a motion of a drive pulley in response to the force against the C-arm exceeding a threshold force and the slip clutch mechanism being in the disengaged state.

13. The system of claim 12, wherein the instructions further enable the controller to determine a collision has occurred in response to the drive pulley being stationary, wherein the controller signals the motor to deactivate, wherein the slip clutch mechanism is returned to the engaged state.

14. The system of claim 12, wherein the instructions further enable the controller to determine a manual operation of the C-arm is occurring in response to the drive pulley moving.

15. The system of claim 12, wherein the drive pulley is engagingly coupled to a belt via a plurality of teeth, and wherein the belt extends to opposite ends of the C-arm.

16. The system of claim 15, wherein a first portion of the arm comprises an X-ray source and a second portion of the C-arm, opposite the first portion, comprises an X-ray detector.

17. The system of claim 12, wherein the engaged state comprises where a drive shaft is coupled to the drive pulley.

18. The system of claim 12, wherein the disengaged state comprises where a drive shaft is uncoupled from the drive pulley.

19. The system of claim 12, wherein the slip clutch mechanism comprises a spring or plurality of springs pressing against a pressure plate or plurality of pressure plates.

\* \* \* \* \*